United States Patent [19]

Tóth et al.

[11] Patent Number: 4,605,672

[45] Date of Patent: * Aug. 12, 1986

[54] DIETHYLAMINOALKOXYBENZHYDROL DERIVATIVES, PROCESS FOR THEIR PREPARATION AND PHARMACEUTICAL COMPOSITIONS CONTAINING THEM

[75] Inventors: Edit Tóth; József Törley; György Fekete; László Szporny; László Vereczkey; Éva Pálosi; Imre Klebovich; Pál Vittay; Sándor Görög; István Hajdu, all of Budapest, Hungary

[73] Assignee: Richter Gedeon Vegyeszeti Gyar Rt., Budapest, Hungary

[*] Notice: The portion of the term of this patent subsequent to Nov. 5, 2002 has been disclaimed.

[21] Appl. No.: 565,912

[22] Filed: Dec. 27, 1983

[30] Foreign Application Priority Data

Dec. 28, 1982 [HU] Hungary .............................. 4182/82

[51] Int. Cl.$^4$ ................. A61K 31/135; A61K 31/205
[52] U.S. Cl. ..................... 514/648; 514/554; 514/643; 564/283; 564/324; 564/327
[58] Field of Search ................ 564/324, 327; 424/316, 424/330; 260/501.12; 514/554, 643, 648

[56] References Cited

U.S. PATENT DOCUMENTS

| | | | |
|---|---|---|---|
| 3,927,128 | 12/1975 | Kyburz et al. | 564/379 X |
| 4,024,282 | 5/1977 | Kikumoto et al. | 564/324 X |
| 4,039,589 | 8/1977 | Toth et al. | 564/327 X |
| 4,094,908 | 6/1978 | Toth et al. | 564/324 |

*Primary Examiner*—Robert V. Hines
*Attorney, Agent, or Firm*—Karl F. Ross; Herbert Dubno

[57] ABSTRACT

The invention relates to the preparation of new diethylaminoalkoxybenzhydrol derivatives of the formula (I)

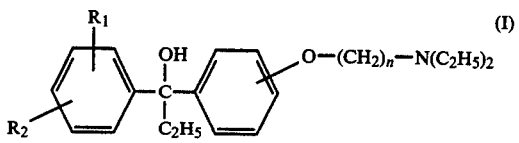

wherein
$R_1$ is hydrogen, halogen, trihalomethyl, alkyl having from one to 4 carbon atoms or alkoxy having from one to 4 carbon atoms,
$R_2$ is halogen, trihalomethyl, or alkoxy having from one to 4 carbon atoms, and
n is 1, 2, 3 or 4, and acid addition and quaternary ammonium salts thereof.

According to another aspect of the invention, there are provided new compounds of the formula (I), and acid addition and quaternary salts thereof. The compounds can be used for the treatment of acute ethanolic intoxication and depression syndromes. Pharmaceutical compositions containing them as active ingredient are also within the scope of the invention.

9 Claims, No Drawings

DIETHYLAMINOALKOXYBENZHYDROL DERIVATIVES, PROCESS FOR THEIR PREPARATION AND PHARMACEUTICAL COMPOSITIONS CONTAINING THEM

This invention relates to new diethylaminoalkoxybenzhydrol derivatives of the formula (I)

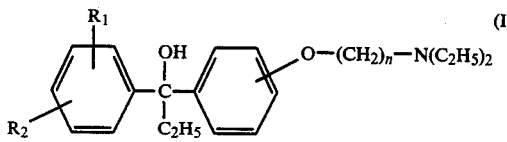

wherein
$R_1$ is hydrogen, halogen, trihalomethyl, akyl having from one to 4 carbon atoms or alkoxy having from one to 4 carbon atoms,
$R_2$ is halogen, trihalomethyl, alkyl having from one to 4 carbon atoms or alkoxy having from one to 4 carbon atoms, and
n is 1, 2, 3 or 4,
and acid addition and quaternary salts thereof, to a process for the preparation thereof and to pharmaceutical compositions containing them as active ingredients.

The term "halogen" as used herein embraces all of the halogens, and may be fluorine, chlorine, bromine or iodine.

The term "alkyl having from one to 4 carbon atoms" refers to straight or branched chained aliphatic hydrocarbon groups containing from one to 4 carbon atoms.

The term "alkoxy having from one to 4 carbon atoms" is used herein to refer to straight or branched chained alkoxy groups containing from one to 4 carbon atoms.

The trihalomethyl groups may contain any of the halogens listed above.

The acid addition salts and quaternary salts of these compounds are also within the scope of the invention.

Compounds of analogous structures are disclosed for example in the following references: C.A. 22, 410[1]; 35, 1781[2]; 4712[5]; P 1015 b; 47, 9548 e; 50. 12390 c; 50. 2509 i; 55, 17915 e; 55, 15413 b; 75, P 103682 b; 76, P 119921 k; 82, 16477 g; 90, 86082 g; 92, 52927 b. None of these citations does, however, mention any pharmaceutical activity of the disclosed compounds.

According to a further aspect of the present invention there is provided a process for the preparation of the compounds of the formula (I), wherein $R_1$, $R_2$ and n have the same meaning as defined above, which process comprises (a) reacting a propiophenone of the formula (II)

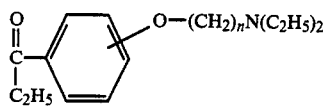

wherein n is as defined above, with an organometallic compound of the formula (III)

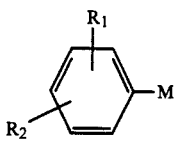

wherein $R_1$ and $R_2$ are as defined above, and
M is an alkali metal, preferably lithium, sodium or potassium, or an MgX group, in which X is halogen;
or
(b) reacting a compound of the formula (IV)

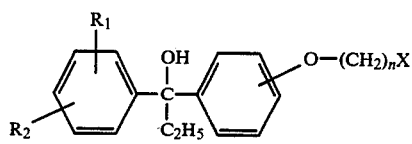

wherein $R_1$, $R_2$ and n are as defined above, and X is halogen, with diethyl amine, preferably in the presence of an acid binding agent; or
(c) reacting a benzophenone of the formula (V)

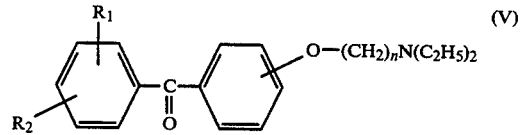

wherein $R_1$, $R_2$ and n are as defined above, with an organometallic compound containing an ethyl moiety, preferably ethylmagnesium halide or ethyl lithium; or
(d) reacting a propiophenone of the formula (VI)

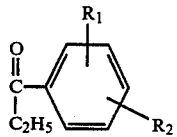

wherein $R_1$ and $R_2$ are as defined above, with a Grignard-compound of the formula (VII)

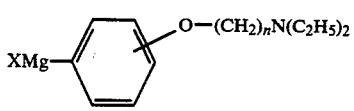

wherein n is as defined above, and
X stands for halogen; or
(e) reacting a compound of the formula (VIII)

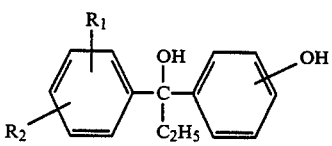

preferably in the form of an alkali metal or quaternary ammonium phenolate thereof, with a tertiary amine of the formula (IX)

$(C_2H_5)_2N-(CH_2)_n-X$ (IX)

or with a salt thereof, wherein in the formula $R_1$ and $R_2$ are as defined above, and X is an alkylsulfonyloxy or arylsulfonyloxy group or halogen, preferably in the presence of an acid binding agent; or (f) reducing a compound of the formula (X)

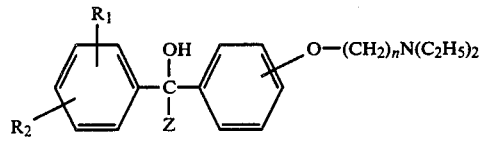

wherein $R_1$, $R_2$ and n are as defined above, and

Z is ethinyl or vinyl, and, if desired, converting any of the free bases obtained by the above-mentioned process variants into their acid addition salts or quaternary ammonium salts, or converting a compound obtained as a salt into the corresponding free base and/or converting a free base obtained into an acid addition or quaternary ammonium salt thereof.

The starting materials are known in the art or can be prepared by well known methods. Ketones of the formulae (II), (V) and (VI) can for example be synthetized by the Friedel-Crafts type ketone synthesis (G. A. Olah: Friedel-Crafts and related reactions, III/1, Ed.: Interscience Publishers (1964), pp. 1–63).

The Grignard compounds of the formulae (III) and (VII) are for example prepared from the corresponding aryl halides by known techniques (M. S. Kharash et al.: Grignard reactions of nonmetallic substances, Ed.: Prentice-Hall. Inc. (1954) pp. 5–90), while the alkali metal-organic compounds can be prepared following the method disclosed in Houben-Weyl: Methoden der Organischen Chemie, XIII/1, pp. 134–159 and 389–405 (1970).

The compounds of the formulae (IV) and (VIII) can for example be synthesized starting from the corresponding propiophenones, by Grignard reactants, following techniques well known in the art (e.g. M. S. Kharash et al.: Grignard reactions of non-metallic substances, Ed.: Prentice-Hall Inc. (1954) pp. 138–143).

Compounds of the formula (X), in which Z represents a vinyl group are for example obtained by reacting a benzophenone of the formula (VI) with a vinylmagnesium halide, while compounds of the formula (X), in which Z is an ethinyl group are easily prepared by ethinylation of a benzophenone of the formula (VI), following the procedure described in the Hungarian Patent Specification No. 166,769.

According to a preferred embodiment of process variant (a) propiophenones of the formula (II) are reacted with the organometallic compounds of the formula (III), preferably with an appropriately substituted phenyl magnesium chloride or bromide or an appropriately substituted phenyl lithium, in an anhydrous inert organic solvent. The reaction is carried out preferably in an aprotic organic solvent, e.g. in an aliphatic ether such as diethyl ether, di-n-butyl ether or diethylene glycol dimethyl ether, an alicyclic ether such as tetrahydrofurane, dioxane, an aliphatic or aromatic hydrocarbon such as ligroin, benzene, toluene, xylene, dimethyl sulfoxide or hexamethyl phosphorus amide, or a mixture of these solvents. The organometallic compound is used in at least equimolar amount. The reaction is preferably performed in an inert gas atmosphere, e.g. in nitrogen or argon. The reaction temperature may range from −60° C. up to the boiling point of the solvent, and preferably is between −30° C. and 100° C. When the reaction is over, the reaction mixture is decomposed, preferably with an aqueous ammonium chloride solution, and the obtained compound of the formula (I) is separated. The product can be purified by known techniques, e.g. by distillation or crystallization.

According to process variant (b) compounds of the formula (IV), in which X preferably represents chlorine or bromine, are reacted with diethyl amine. The reaction is preferably accomplished in an organic solvent, in the presence of a base suitable for binding the acid formed in the reaction. As a solvent for example hydrocarbons such as ligroin, benzene, toluene, halogenated hydrocarbons such as chloroform, ethers such as dioxane, alcohols such as ethanol, esters such as ethyl acetate, acid amides such as dimethyl formamide, ketones such as acetone or methyl isobutyl ketone, or a mixture of these solvents can be employed. If the excess of diethyl amine or a tertiary organic base is used to bind the hydrogen halide formed in the course of the reaction, these may well serve as a solvent, too. The reaction is carried out at a temperature between 20° C. and the boiling point of the solvent. After termination of the reaction the product is isolated, e.g. by pouring the reaction mixture onto water, and separating the product by solvent extraction. The organic phase is washed halogen-free with water, dried and evaporated. The crude product can be purified for instance by distillation or crystallization.

According to process variant (c) a benzophenone of the formula (V) is preferably reacted with an at least equimolar amount of ethyl magnesium bromide or ethyl magnesium iodide or ethyl lithium. The reaction is accomplished in an inert anhydrous organic solvent, essentially as described in connection with process variant (a).

According to process variant (d) the Grignard compounds of the formula (VII), in particular those in which X is bromine, are reacted with an at least equimolar amount of propiophenones of the formula (VI), in an anhydrous inert organic solvent, similarly to process variant (a).

According to a preferred embodiment of process variant (e) compounds of the formula (VIII) in the form of their alkali metal or quaternary ammonium phenolates are condensed with the tertiary amines of the formula (IX). As a tertiary amine e.g. diethylaminoalkyl mesylate, tosylate, bromide or preferably chloride is employed, as a free base or a salt, e.g. hydrogen halide thereof. The reaction is preferably carried out in an inert organic solvent, in the presence of an acid binding agent, under anhydrous conditions or in a mixture of water and an organic solvent. As organic solvents for example esters such as ethyl acetate, ethers such as dioxane, tetrahydrofurane or diethyl ether, hydrocarbons such as ligroin, benzene, toluene or xylene, halogenated hydrocarbons such as chloroform, chlorobenzene, acid amides such as dimethyl formamide, ketones such as acetone, methyl ethyl ketone or methyl isobutyl ketone, alcohols such as ethanol, propanol, etc. are employed. Compounds of the formula (VIII) can be converted into their phenolates by methods known in the art, e.g. with alkali metal alcoholates, amides, hydrides, hydroxides, carbonates or quaternary ammonium compounds. Preferred acid binding agents include inorganic and tertiary organic bases, e.g. sodium hydroxide, potassium hydroxide, potassium carbonate, triethyl amine, pyridine, etc. The reaction is optionally performed in the presence of a catalyst. As a catalyst for example alkali metal halides, preferably alkali metal iodide may be used. The reaction temperature may be varied within a wide range, and preferably is between 20° C. and the boiling point of the solvent.

According to process variant (f) the ethinyl or vinyl compounds of the formula (X) are preferably reduced by catalytic hydrogenation. Suitable hydrogenation catalysts include metals such as ruthenium, palladium, platinum, nickel, iron, copper, cobalt, chromium, zinc, molybdenum, tungsten, etc. and the oxides and sulfides of these metals. The catalysts may be prepared by reducing their stable oxides with hydrogen, directly in the reaction vessel. This procedure is especially suitable for the preparation of a finely dispersed platinum or palladium catalyst. The catalytic hydrogenation may be accomplished also in the presence of catalysts precipitated on the surface of a carrier, e.g. charcoal, silica, alumina or sulfates or carbonates of the alkali earth metals. The reaction may be carried out also in the presence of a Raney-nickel catalyst. The catalytic hydrogenation is preferably performed in the presence of palladium, in particular palladium-on-charcoal or Raney-nickel, in an organic solvent inert under the reaction conditions. As a solvent for example lower aliphatic alcohols, ethers, esters, aliphatic, cycloaliphatic and aromatic hydrocarbons or mixtures of these solvents may be employed. The hydrogenation may be carried out under atmospheric or higher pressure, preferably not exceeding 506 kPa, at a temperature between 20° C. and the boiling point of the solvent employed. The reduction is preferably carried out at room temperature, under atmospheric pressure until ceasing of the hydrogen uptake. The catalyst is then filtered off, the filtrate is evaporated, and if desired, the product is purified e.g. by distillation or crystallization.

If desired, the compounds of the formula (I) can be converted into their acid addition salts or quaternary ammonium salts by methods well known in the art. The acid addition salts can be prepared by means of inorganic or organic acids, e.g. hydrogen halides such as hydrochloric acid, hydrogen bromide, etc., sulfuric acid, phosphoric acids, formic acid, acetic acid, propionic acid, oxalic acid, glycolic acid, maleic acid, fumaric acid, tartaric acid, succinic acid, ascorbic acid, citric acid, malic acid, salicylic acid, lactic acid, benzoic acid, cinnamic acid, asparaginic acid, glutaminic acid, N-acetyl-asparaginic acid, N-acetyl-glutaminic acid, alkylsulfonic acids such as methanesulfonic acid, arylsulfonic acids such as p-toluene-sulfonic acid, etc. According to a preferred embodiment the corresponding acid is added to a solution of a compound of the formula (I) in an inert solvent, e.g. ethanol, and the salt formed is precipitated, preferably with a water-immiscible organic solvent such as diethyl ether. Quaternization is preferably carried out with a lower alkyl, alkenyl or benzyl halide or alkyl sulfate. The reaction is performed in an organic solvent, preferably acetone, acetonitrile, ethanol or in a mixture thereof, at a temperature between room temperature and the boiling point of the solvent. The quaternary salts can be isolated e.g. by filtration and if desired, are purified by crystallization.

The new compounds of the formula (I) and their salts possess valuable pharmacological properties. More particularly, these compounds shorten the duration of ethyl alcoholic narcosis and are potent antidepressants, therefore can successfully be used in the therapy for the treatment of alcoholic intoxication or depression symptomes.

The effect of the compounds according to the invention on ethanolic narcosis was tested on male and female Wistar rats, each weighing 160 to 180 g., in groups of 10. The animals were fasted for 16 hours prior to treatment and were then administered various doses of the test compound, orally. One hour after treatment the rats were treated with 3.5 g./kg. of ethanol intraperitoneally (i.p.). The narcosis period of the animals was measured from the elapse of the righting reflex until a spontaneous correction of the body position. The average of the narcosis period and the percentage difference from the control were calculated. As a reference material L-cysteine was employed, which is known to have an alcoholic narcosis reducing effect. The control group was treated with a placebo and a 3.5 mg./kg. dose of ethanol. The results are shown in Table 1.

Abbreviations:
$\bar{x} \pm S.E.$ = mean value ± standard error,
n = number of the animals,
A = 3-trifluoromethyl-4'-[3-(diethylamino)-propoxy]-α-ethyl-benzhydrol,
B = 4-chloro-4'-[2-(diethylamino)-ethoxy]-α-ethyl-benzhydrol.

TABLE I

| Compound | Dose (mg./kg.) | Ethanolic narcosis period (Control ± S.E. %) | n |
|---|---|---|---|
| A | 10.0 | 52 ± 11.1 | 10 |
|  | 40.0 | 40 ± 5.0 | 10 |
| B | 10.0 | 48 ± 9.5 | 10 |
|  | 40.0 | 39 ± 4.5 | 10 |
| L-cysteine | 500.0 | 63 ± 4.2 | 10 |
| Control° |  | 100 ± 6.5 | 10 |

°Narcosis period for the control: 83.0 ± 5.44
($\bar{x} \pm$ S.E.) min.

The effect of the compounds on hyperactivity induced by ethanol was tested on male and female BALB/c mice, each weighing 16 to 18 g. The test materials were administered to groups of 15 orally, one hour before administering the placebo orally or a 2 g./kg. dose of ethanol intraperitoneally. The control animals were treated with the placebo. The locomotor activity of the animals was measured for two hours, using an Animex BSE motimeter. The results, expressed in percentage of the control are summarized in Table 2.

TABLE 2

| Compound | Dose (mg./kg.) Compound | Dose (mg./kg.) Ethanol | Locomotor activity (2 hours) | n |
|---|---|---|---|---|
| Control treated with placebo° | — | — | 100 ± 8.1 | 15 |
| Ethanol + Placebo | — | 2000.0 | 190 ± 12.2 | 15 |
| B + Placebo | 10.0 | — | 110 ± 15.2 | 15 |
| B + Ethanol | 10.0 | 2000.0 | 110 ± 8.1 | 15 |

°Control treated with placebo $\bar{x} \pm$ S.E. = 3040.5 ± 246.24 locomotor activity/2 hours The effect of the compounds according to the invention on ethanolic ataxia and the change of muscular tension was tested on rotating rods. Trained and selected male and female BALB/c mice weighing 16 to 18 g. each were administered a 40 mg./kg. oral dose of the test compounds one hour before intraperitoneal administration of 2.5 g./kg. of ethanol. The time until the animals could remain on the rod was measured 60, 90 and 120 minutes after the ethanolic treatment. This time was 120 minutes for the animals with intact coordination. The results are summarized in Table 3, where the percentage of the animals remaining on the rotating rod is indicated.

TABLE 3

| Compound | Dose (mg./kg.) | % of the animals remaining on the rod minutes | | | n |
|---|---|---|---|---|---|
| | | 60 | 90 | 120 | |
| Ethanol | — | 2500.0 | 10 | 40 | 50 | 10 |
| B + Ethanol | 40.0 | 2500.0 | 40 | 70 | 90 | 10 |
| B | 40.0 | — | 100 | 100 | 100 | 10 |

To determine the antidepressive activity of the compounds provided by the invention the inhibition of catalepsy induced by tetrabenazine and the inversion of hypothermia induced by reserpin were measured. The anticholinergic activity was tested by determining the inhibition of tremor induced by oxotremorin. As a reference compound imipramine was used.

To determine the inhibition of catalepsy induced by tetrabenazine Hann.-Wistar rats weighing 150 to 160 g. each were treated with various doses of the test compounds orally, 60 minutes before intraperitoneal administration of a 30 mg./kg. dose of tetrabenazine. The inhibition of catalepsy was monitored for 3 hours after tetrabenazine administration In Table 4 the $ED_{50}$-values calculated from the percentage of non-cataleptic animals by probitanalysis are set forth.

The inversion of reserpin-hypothermia was tested on male CFLP mice, weighing 18 to 22 g. each and treated with a 5 mg./kg. dose of reserpin intraperitoneally. 16 hours after treatment the animals were administered various doses of the test compounds, orally. The rectal temperature of the animals was measured before the reserpin treatment, 16 hours after treatment and 2 hours after the administration of the test compounds. In Table 4 the dose increasing the body temperature of the animals by 50% ($ED_{50}$) is indicated.

The anticholinergic activity was tested on male CFLP mice, weighing 18 to 22 g. each, which were treated with a 0.5 mg./kg. dose of oxotremorin (i.p.) and after 60 minutes with various oral doses of the test compounds. The $ED_{50}$-values are set forth in Table 4.

The acute toxicity of the compounds according to the invention was determined on Hann.-Wistar rats of both sexes, weighing 160 to 180 g. each, which had been treated with a single 500 mg./kg. dose of the test compounds, orally. The animals were observed for 14 hours after treatment. In Table 4 the percentage of the dead animals is given.

C=4-trifluoromethyl-4'-[2-(diethylamino)-ethoxy]-α-ethyl-benzhydrol

D=3-chloro-4'-[3-(diethylamino)-propoxy]-α-ethyl-benzhydrol

TABLE 4

| Compound | Inhibition of catalepsy ($ED_{50}$ mg./kg.) | Antireserpin activity ($ED_{50}$ mg./kg.) | Oxotremorin inh. ($ED_{50}$ mg./kg.) | Toxicity Dead animals (%) |
|---|---|---|---|---|
| C | 20.0 | 30.0 | 160.0 (ineffective) | 0 |
| D | 18.8 | 17.0 | 160.0 (ineffective) | 0 |
| Imipramine | 13.7 | 15.0 | 50.0 | 80 |

As appears from the pharmacological data, the compounds provided by the invention are potent antagonizers of the central nervous system depressing and stimulating activity of ethanol. They substantially shorten the alcoholic narcosis period, and their activity is the same or higher than the activity of L-cystein used as a reference compound, when administered in a 50-times smaller dose. The compounds according to the invention normalize the ethanolic hyperactivity, have no influence on the locomotor activity, while effectively reduce ataxia. Their antidepressive activity is in the same order of magnitude as that of imipramine, but they are devoid of the side-effect, e.g. anticholinergic activity characteristic of the tricyclic antidepressants such as imipramine. Their toxicity is lower than that of imipramine.

The pharmacologically active compounds according to the invention can be used in therapy in the form of pharmaceutical compositions, which are formulated as preparations suitable for oral, rectal and/or parenteral administration. For oral administration tablets, dragées or capsules are prepared. The oral formulations contain as a vehicle e.g. lactose or starch, as an excipient or a granulation aid e.g. gelatine, carboxymethyl cellulose sodium, methyl cellulose, polyvinyl pyrrolidone or starch gum, as a disintegrating substance e.g. potato starch or microcrystalline cellulose, ultraamylopectine or formaldehyde casein, etc. The formulations may also contain antiadhesives and lubricants such as talc, colloidal silica, stearine, calcium or magnesium stearate, etc.

Tablets are prepared for example by wet granulation and subsequent pressing. A mixture of the active ingredient and the vehicle and optionally a part of the disintegrating agent is granulated with an aqueous, alcoholic or aqueous-alcoholic solution of the excipients in a suitable equipment, and the granulate is dried. The remaining portions of the disintegrating substance, lubricant, anti-adhesive or optional further additives are then added to the granules, and the mixture is pressed to tablets. If desired, the tablets are prepared with a dividing line, which facilitates administration. Tablets can be prepared also from a mixture of the active ingredient and suitable additives by direct pressing.

If desired, the tablets can be converted into dragées, using protecting, flavoring agents and pigments generally known for the preparation of pharmaceutical compositions, e.g. sugar, cellulose derivatives (methyl or ethyl cellulose, carboxymethyl cellulose sodium, etc.), polyvinylpyrrolidone, calcium phosphate, calcium carbonate, food pigments, food oil varnishes, aroma substances, iron oxide pigments, etc.

Capsules are prepared by filling a mixture of the active ingredients and the additives into suitable capsules.

For rectal administration the compositions are formulated as suppositories, which contain in addition to the active ingredient a carrier mass, called adeps pro suppository. Suitable carriers include vegetable fats, e.g. hardened vegetable oils, triglycerides of fatty acids having 12 to 18 carbon atoms, preferably Witepsol (a registered trade mark). The active ingredient is homogeneously distributed in the melted carrier mass, and suppositories are prepared by casting.

For parenteral administration injectable preparations are prepared. To prepare an injectable solution the active ingredient is dissolved in dist. water and/or various organic solvents, e.g. glycol ethers, optionally in the presence of dissolution aids, e.g. polyoxyethylene sorbitane monolaurate, monooleate or monostearate (Tween 20, Tween 60, Tween 80). The injectable solutions may contain also various additives, e.g. preserving agents, such as benzyl alcohol, p-oxy-benzoic acid methyl or propyl ester, benzalkonium chloride or phenyl mercuri borate, etc., antioxidants such as ascorbic acid, tocopherol, sodium pyrosulfate and optionally complexing agents to bind metal traces such as ethylene diamine tetraacetate, buffers to adjust the pH and optionally local anaesthetics such as lidocaine. The injectable solutions are filtered, filled into ampoules and sterilized. The daily dose, depending on the state of the patient, varies between 0.1 and 300 mg./kg., preferably 2.0 and 160 mg./kg, preferably in more, smaller portions a day.

The daily dose of antidepressive compounds generally is between 0.5 and 100.0 mg./kg, depending on the state of the patient, and a single dose preferably is 1.5 to 20.0 mg./kg.

The invention will be further illustrated by the following Examples but it is not intended to limit the scope of the invention to the Examples.

EXAMPLE 1

3-Trifluoromethyl-4'-[3-(diethylamino)-propoxy]-α-ethyl-benzhydrol

To a Grignard reactant prepared from 3.7 g. of magnesium turnings and 33.8 g. of 3-bromobenzotrifluoride in 100 ml. of tetrahydrofurane a solution of 26.3 g. of 4-[3-(diethylamino)-propoxy]-propiophenone in 60 ml. of tetrahyrofurane is added dropwise, with stirring under slight reflux. The reaction mixture is slightly boiled for 30 additional minutes, whereupon it is cooled and poured onto saturated aqueous ammonium chloride solution. The aqueous phase is extracted with tetrahydrofurane. The tretrahydrofurane phases are combined and washed with a saturated aqueous sodium chloride solution. After drying over anhydrous magnesium sulfate, the solvent is evaporated under reduced pressure, and the residue is distilled in vacuo to yield 24.4 g. of the title compound, boiling at 186° to 188° C./13.3 Pa. Melting point: 44° to 46° C.

Analysis for $C_{23}H_{30}F_3NO_2$: Calculated: C 67.46%, H 7.38%, F 13.92%, N 3.42%; Found: C 67.57%, H 7.33%, F 14.10%, N 3.58%.

Upon addition of hydrochloric acid in ether to an ethereal solution of the base under cooling the hydrochloride of the base precipitates in a crystalline form, which is then filtered off, washed with ether and dried. Melting point: 141° to 143°.

If an ethanolic solution of the base is treated with an ethanolic solution of citric acid, and to the solution obtained ether is added, dihydrogen citrate of the base is obtained as a precipitate, which is then filtered off, washed with ether and dried to yield a product melting at 62° C.

Similarly there can be prepared the following compounds by proper selection of the starting substances.

2-Methoxy-4'-[2-(diethylamino)-ethoxy]-α-ethyl-benzhydrol, melting point: 51°–52° C.

Analysis for $C_{22}H_{31}NO_3$: Calculated: C 73.91%, H 8.74%, N 3.92%; Found: C 73.83%, H 8.83%, N 4.11%.

4-Trifluoromethyl-4'-[2-(diethylamino)-ethoxy]-α-ethyl-benzhydrol, melting point: 56°–57° C.

Analysis for $C_{22}H_{28}F_3NO_2$: Calculated C 66.81%, H 7.14%, F 14.41%, N 3.54%; Found: C 66.83%, H 7.22%, F 14.60%, N 3.67%.

Melting point of hydrochloride: 152°–153° C.
Melting point of dihydrogen citrate: 110°–111° C.

EXAMPLE 2

3-Chloro-4'-[3-(diethylamino)-propoxy]-α-ethyl-benzhydrol 19.2 g. of 3-chloro-4'-(3-bromopropoxy)-α-ethyl-benzhydrol and 51 ml. of dipropyl amine are refluxed for 8 hours, and the reaction mixture is then evaporated in vacuo. To the residue water is added and it is extracted with benzene. The benzene phase is washed with water, dried over anhydrous magnesium sulfate, and the solution is evaporated under reduced pressure. Distillation of the residue in vacuo yields 11.5 g. of the title compound, boiling at 203° to 206° C./13.3 Pa.

Analysis for $C_{22}H_{30}ClNO_2$: Calculated: C 70.28%, H 8.04%, Cl 9.43%, N 3.73%; Found: C 70.35%, H 8.15%, Cl 9.35, N 3.84%.

Melting point of the dihydrogen citrate: 59° to 60° C.

EXAMPLE 3

3-Chloro-4'-[2-(diethylamino)-ethoxy]-α-ethyl-benzhydrol

To 125 ml. of a 0.8 molar ethereal ethyl lithium solution a solution of 13.3 g. of 3-chloro-4'-[2-(diethylamino)-ethoxy]-benzophenone in 160 ml. of ether is added dropwise, with stirring under argon atmosphere, at a temperature between −20° C. and −15° C. The reaction mixture is then stirred at room temperature for one hour, and is decomposed with a saturated aqueous ammonium chloride solution, under cooling. The aqueous phase is extracted with ether, the ethereal phases are combined and washed to neutral with water. After drying over anhydrous magnesium sulfate, ether is distilled off under reduced pressure. Crystallization of the solid residue from n-hexane yields 8.9 g. of the title compound, melting at 64° to 65° C.

Analysis for $C_{21}H_{28}ClNO_2$: Calculated: C 69.69%, H 7.80%, Cl 9.80%, N 3.87%; Found: C 69.77%, H 7.85%, Cl 9.94%, N 3.98%.

EXAMPLE 4

4-Fluoro-4'-[3-(diethylamino)-propoxy]-α-ethyl-benzhydrol

To a Grignard reactant prepared from 2.4 g. of magnesium turnings and 28.6 g. of 4-[3-(diethylamino)-propoxy]-bromobenzene in 100 ml. of dry tetrahydrofurane a solution of 12.2 g. of 4-fluoropropionophenone in 60 ml. of tetrahydrofurane is added dropwise, at 20° C. The reaction mixture is slightly boiled for one hour, cooled and poured onto a 20% aqueous ammonium chloride solution. Tetrahydrofurane is distilled off under reduced pressure and the residue is extracted with benzene. The benzene phase is washed to neutral with water, dried over anhydrous magnesium sulfate, filtered and the filtrate is evaporated under reduced pressure. The residue is distilled in vacuo to yield 19.5 g. of the title compound, boiling at 193° to 195° C./13.3 Pa.

Analysis for $C_{22}H_{30}FNO_2$: Calculated: C 73.50%, H 8.41%, F 5.28%, N 3.90%; Found: C 73.66%, H 8.51%, F 5.43%, N 3.81%.

Melting point of the dihydrogen citrate: 64° to 66° C.

EXAMPLE 5

2-Methoxy-4'-[3-(diethylamino)-propoxy]-α-ethyl-benzhydrol 12.9 g. of 2-methoxy-4'-hydroxy-α-ethyl-benzhydrol are dissolved in 100 ml. of methyl isobutyl ketone, 23 g. of anhydrous potassium carbonate 0.4 ml. of a 40% tetrabutyl ammoniumhydroxide solution and 10.3 g. of 3-diethylamino-propyl chloride hydrochloride are added, and the solution is heated up to the boiling point. The reaction mixture is boiled for 4 hours, and the solvent is distilled off under reduced pressure. To the residue water is added, and it is extracted with benzene. The benzene phase is washed with a 5% potassium hydroxide solution and subsequently with water. After drying over anhydrous potassium carbonate, benzene is distilled off under reduced pressure, and the residue is fractionated in vacuo to yield 13.2 g. of the title compound, boiling at 200° to 203° C./13.3 Pa.

Analysis for $C_{23}H_{33}NO_3$: Calculated: C 74.35%, H 8.95%, N 3.77%; Found: C 74.48%, H 9.14%, N 3.69%.

Melting point of dihydrogen citrate: 79° C.

EXAMPLE 6

2,5-Dimethyl-4'-[2-(diethylamino)-ethoxy]-α-ethyl benzhydrol 10.5 g. of 2,5-dimethyl-4'-[2-(diethylamino)-ethoxy]-α-ethinyl-benzhydrol are dissolved in 110 ml. of methanol, and 0.5 g. of a 10% palladium-on-charcoal catalyst are added to the mixture. The reaction mixture is hydrogenated until the uptake of the calculated amount of hydrogen is complete. Thereafter the catalyst is filtered off, and the solvent is evaporated in vacuo. Recrystallization of the solid residue obtained from a mixture of n-hexane and ethyl acetate yields 9.1 g. of the title compound, melting at 89° to 90° C.

Analysis for $C_{23}H_{33}NO_2$: Calculated: C 77.70%, H 9.35%, N 3.94%; Found: C 77.64%, H 9.51%, N 4.11%.

EXAMPLE 7

4-Chloro-4'-[3-(diethylamino)-propoxy]-α-ethyl-benzhydrol

To a Grignard reactant prepared from 7.2 g. of magnesium turnings and 32.6 g. of ethyl bromide in 120 ml. of dry ether a solution of 25.6 g. of 4-chloro-4'-[3-(diethylamino)-propoxy]-benzophenone in 300 ml. of dry ether is added dropwise, with stirring at −30° C. The reaction mixture is refluxed for 30 minutes. After cooling, it is poured onto a solution of ammonium chloride in ice water. The aqueous phase is extracted with ether, the ethereal phase is washed to neutral with water, dried over anhydrous magnesium sulfate, and the solvent is evaporated under reduced pressure. Distillation of the residue in vacuo yields 15.3 g. of the title compound, boiling at 212° to 214° C./13.3 Pa.

Analysis for $C_{22}H_{30}ClNO_2$: Calculated: C 70.28%, H 8.04%, Cl 9.43%, N 3.73%; Found: C 70.33%, H 8.11%, Cl 9.51%, N 3.85%.

Melting point of the dihydrogen citrate: 62° to 63° C.

EXAMPLE 8

3-Trifluoromethyl-4'-[2-(diethylamino)-ethoxy]-α-ethyl-benzhydrol

To 250 ml. of a 0.4 molar solution of 3-trifluoromethylphenyl-lithium in ether a solution of 6.3 g. of 4'-[2-(diethylamino)-ethoxy]-propionphenone in 60 ml. of dry ether is added dropwise, under argon atmosphere, at −30° C., and the reaction mixture is stirred at room temperature for two hours. After cooling the reaction mixture is decomposed with a saturated, aqueous ammonium chloride solution, and the aqueous phase is extracted with ether. The ethereal phases are combined, washed to neutral with water and dried over anhydrous magnesium sulfate. Ether is distilled off under reduced pressure. The residue is chromatographed on a silica gel column with a 7:3 mixture of benzene and ethyl acetate. The solvent mixture is distilled in vacuo, and the residue is crystallized from n-hexane. 3.2 g. of the title compound are obtained, melting at 74° to 75° C.

Analysis for $C_{22}H_{28}F_3NO_2$: Calculated: C 66.81%, H 7.14%, F 14.41%, N 3.54%; Found: C 66.93%, H 7.03%, F 14.58%, N 3.41%.

EXAMPLE 9

4-Chloro-4'-[2-(diethylamino)-ethoxy]-α-ethyl-benzhydrol 17.9 g. of 4-chloro-4'-[2-(diethylamino)ethoxy]-α-ethinyl-benzhydrol are dissolved in 180 ml. of benzene, and the reaction mixture is hydrogenated in the presence of 0.9 g. of a 10% palladium-on-charcoal catalyst. As soon as the uptake of the calculated amount of hydrogen is complete, the catalyst is filtered off, and benzene is distilled off under reduced pressure. The solid residue is crystallized from n-hexane to yield 14.2 g. of the title compound, melting at 50° to 51° C.

Analysis for $C_{21}H_{28}ClNO_2$: Calculated: C 69.69%, H 7.80%, Cl 9.80%, N 3.87%; Found: C 69.75%, H 7.78%, Cl 9.91%, N 3.77%.

Melting point of the corresponding hydrochloride: 153°–154° C.

Melting point of dihydrogen citrate: 97°–98° C.

Melting point of hydrogen fumarate: 71°–73° C.

EXAMPLE 10

4-Chloro-4'-[2-(diethylamino)-ethoxy]-α-ethyl-benzhydrol ethoidide 3.6 g. of 4-chloro-4'-[2-(diethylamino)ethoxy]-α-ethyl-benzhydrol and 1.2 ml. of ethyl iodide are dissolved in 18 ml. of dry acetone, and the reaction mixture is slightly boiled under reflux for two hours. After cooling the mixture is diluted with ether, and the crystalline product is filtered off and dried. 4.3 g. of the title compound are obtained, melting at 143° to 144° C.

Similarly is obtained 4-trifluoromethyl-4'-[2-(diethylamino)-ethoxy]-α-ethyl-benzhydrolethoiodide by proper selection of starting substances. Melting point: 167° to 168° C.

EXAMPLE 11

The new compounds according to the invention can be converted for example into the following pharmaceutical compositions.

Tablets

Composition of a single tablet:
active ingredient: 100.0 mg.
lactose: 184.0 mg.
potato starch: 80.0 mg.
polyvinyl pyrrolidone: 8.0 mg.
talc: 12.0 mg.
magnesium stearate: 2.0 mg.
aerosil (colloidal silica): 2.0 mg.
utraamylopectine: 12.0 mg.

From the ingredients 400-mg. tablets are prepared by wet granulation and subsequent pressing.

Active ingredient: 4-trifluoromethyl-4'-[2-(diethylamino)-ethoxy]-α-ethyl-benzhydrol

Dragées

Tablets as described above are coated with a coating prepared from sugar and talc in a known manner. Dragées are polished with a mixture of bee wax and carnauba wax. Weight of a dragée: 500.0 mg.

Capsules

Composition of a capsule:
active ingredient: 50.0 mg.
lactose: 100.0 mg.
talc: 2.0 mg.
potato starch: 30.0 mg.
cellulose (microcrystalline): 3.0 mg.

The active ingredient and the additives are thoroughly blended, the mixture is passed through a 0.32-mm. sieve and filled into No. 4 hard gelatine capsules.

Active ingredient: 4-chloro-4'-[2-(diethylamino)-ethoxy]-α-ethyl-benzhydrol

Suppositories

Composition of a suppository:
active ingredient: 100.0 mg.
lactose: 200.0 mg.
basic substance of suppository (e.g. Witepsol H): 1700.0 mg.

The basic substance is melted and then cooled to 35° C. The active ingredient is thoroughly admixed with the lactose, and the mixture is homogenized in the basic substance with a suitable equipment. The obtained mass is poured into cool moulds. One suppository weights 2000 mg.

Active ingredient: 3-trifluoromethyl-4'-[3-(diethylamino)-propoxy]-α-ethyl-benzhydrol

Suspensions

Composition of 100 ml. of suspension:
active ingredient: 1.0 g.
sodium hydroxide: 0.26 g.
citric acid: 0.30 g.
nipagin (4-hydroxy-benzoic acid methylester sodium salt): 0.10 g.
Carbopol 940 (polyacrylic acid): 0.30 g.
ethanol (96%): 1.00 g.
raspberry aroma: 0.60 g.
sorbite (70% aqueous solution): 71.00 g.
distilled water up to: 100.0 ml.

To a solution of nipagin and citric acid in 20 ml. of distilled water Carbopol is added in small portions, with vigorous stirring, and the solution is allowed to stand for 10 to 12 hours. Thereafter a solution of the above amount of sodium hydroxide in 1 ml. of distilled water is added dropwise, followed by dropwise addition of an aqueous solution of sorbite and an ethanolic raspberry aroma solution, with stirring. Active ingredient is added in small portions, and the mixture is homogenized. The suspension is supplemented with distilled water ad 100 ml., and the suspension syrup is passed through a colloidal mill.

Active ingredient: 3-chloro-4'-[3-(diethylamino)-propoxy]-α-ethyl-benzhydrol.

We claim:

1. Diethylaminoalkoxybenzhydrol derivatives of the formula (I)

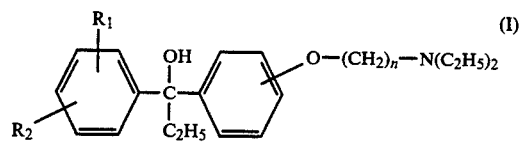

wherein
$R_1$ is hydrogen, halogen, trihalomethyl, alkyl having from one to 4 carbon atoms or alkoxy having from one to 4 carbon atoms,
$R_2$ is halogen, trihalomethyl, or alkoxy having from one to 4 carbon atoms, and
n is 1, 2, 3 or 4,
and a pharmaceutically acceptable acid addition and quaternary salts thereof.

2. A compound of the Formula (I)

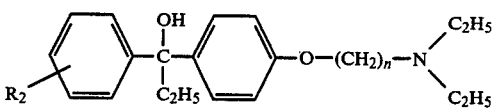

wherein $R_2$ is halogen, trifluoromethyl, or $C_1$ to $C_4$ alkoxy; and n is 2 or 3 or a pharmaceutically acceptable acid addition or quaternary ammonium salt thereof.

3. The compound of the Formula (1) defined in claim 2 and selected from the group consisting of:
(a) 3-trifluoromethyl-4'-[3-(diethylamino)-propoxy]-α-ethyl-benzhydrol;
(b) 2-methoxy-4'-[2-(diethylamino)-ethoxy]-α-ethyl-benzhydrol;
(c) 4-trifluoromethyl-4'-[2-diethylamino)-ethoxy]-α-ethyl-benzhydrol;
(d) 3-chloro-4'-[3-(diethylamino)-propoxy]-α-ethyl-benzhydrol;
(e) 3-chloro-4'-[2-(diethylamino)-ethoxy]α-ethyl-benzhydrol;
(f) 4-fluoro-4'-[3-(diethylamino)-propoxy]-α-ethyl-benzhydrol;
(g) 2-methoxy-4'-[3-(diethylamino)-propoxy]-α-ethyl-benzhydrol;
(h) 4-chloro-4'-[3-(diethylamino)-propoxy]-α-ethyl-benzhydrol;
(i) 3-trifluoromethyl-4'-[2-(diethylamino)-ethoxy]-α-ethyl-benzhydrol; and
(j) 4-chloro-4'-[2-(diethylamino)-ethoxy]-α-ethyl-benzhydrol, or a pharmaceutically acceptable acid addition or quaternary ammonium salt thereof.

4. A pharmaceutical composition for the treatment of ethanolic intoxication containing a pharmaceutically effective amount of a compound of the formula (I) as claimed in claim 1, or a pharmaceutically acceptable acid addition or quaternary ammonium salt thereof, together with a pharmaceutically acceptable carrier or auxiliary substance.

5. A method of treating ethanol intoxication narcosis and depression which comprises administering to a susceptible subject an effective amount of a compound as defined in claim 1.

6. 3-trifluoromethyl-4'-[3-(diethylamino)-propoxy]-α-ethyl-benzhydrol as defined in claim 1.

7. 4-chloro-4'-[2-(diethylamino)-ethoxy]-α-ethyl-benzhydrol as defined in claim 1.

8. 4-trifluoromethyl-4'-[2-(diethyl-amino)-ethoxy]-α-ethyl-benzhydrol as defined in claim 1.

9. 3-chloro-4'-[3-(diethylamino)-propoxy]-α-ethyl-benzhydrol as defined in claim 1.

* * * * *